US011609225B2

(12) United States Patent
Willkomm et al.

(10) Patent No.: US 11,609,225 B2
(45) Date of Patent: Mar. 21, 2023

(54) BREATH ALCOHOL CONTENT DEVICE SECURITY AND SENSING

(71) Applicant: LIFELOC TECHNOLOGIES, INC., Wheat Ridge, CO (US)

(72) Inventors: Wayne Robert Willkomm, Wheat Ridge, CO (US); Mark Anthony Lary, Wheat Ridge, CO (US)

(73) Assignee: LIFELOC TECHNOLOGIES, INC., Wheat Ridge, CO (US)

( * ) Notice: Subject to any disclaimer, the term of this patent is extended or adjusted under 35 U.S.C. 154(b) by 445 days.

(21) Appl. No.: 16/738,967

(22) Filed: Jan. 9, 2020

(65) Prior Publication Data

US 2020/0225211 A1 Jul. 16, 2020

Related U.S. Application Data

(60) Provisional application No. 62/790,902, filed on Jan. 10, 2019.

(51) Int. Cl.
*G01N 33/00* (2006.01)
*G01N 1/22* (2006.01)
*G01N 33/497* (2006.01)

(52) U.S. Cl.
CPC ..... *G01N 33/4972* (2013.01); *G01N 33/0008* (2013.01); *G01N 2001/2244* (2013.01)

(58) Field of Classification Search
CPC ........... G01N 33/4972; G01N 33/0008; G01N 2001/2244
See application file for complete search history.

(56) References Cited

U.S. PATENT DOCUMENTS

| 5,531,225 | A | * | 7/1996 | Nawata .............. G01N 33/4972 340/576 |
| 6,596,153 | B1 | | 7/2003 | Traylor, III |
| 7,287,617 | B2 | | 10/2007 | Mobley et al. |
| 8,418,523 | B2 | | 4/2013 | Lueck et al. |
| 9,562,883 | B2 | | 2/2017 | Knott et al. |
| 2011/0102182 | A1 | | 5/2011 | Ohya |

(Continued)

FOREIGN PATENT DOCUMENTS

JP 2010175320 8/2010

OTHER PUBLICATIONS

Search report for International Application PCT/US2020/012980, dated May 7, 2020.

*Primary Examiner* — Christopher Adam Hixson
(74) *Attorney, Agent, or Firm* — Holzer Patel Drennan (57) ABSTRACT

Electrochemical sensors commonly used in breath alcohol testing devices detect a concentration of alcohol in a sample of fluid. The sample of fluid is introduced into the electrochemical sensor and a current is generated by the oxidation of the alcohol within the fluid. The electrical output from the electrochemical sensor, plotted over time, forms an output curve, which may be used to estimate the concentration of alcohol in the fluid sample. The technology disclosed herein includes various methods for determining the quantity of an electrochemically convertible substance in a fluid sample using a breath alcohol content device, including detecting water saturation level of the fluid sample. The disclosed technology involves measuring electrochemical sensor outputs to quantify alcohol content of the fluid sample.

25 Claims, 6 Drawing Sheets

(56) References Cited

U.S. PATENT DOCUMENTS

2015/0025407 A1    1/2015   Eichler et al.
2016/0022172 A1    1/2016   Frandsen
2018/0074030 A1    3/2018   DeVries et al.

* cited by examiner

FIG. 6

BREATH ALCOHOL CONTENT DEVICE SECURITY AND SENSING

CROSS-REFERENCE TO RELATED APPLICATIONS

The present application claims benefit of priority to U.S. Provisional Patent Application No. 62/790,902 entitled "Breath Alcohol Tester Security and Sensing" and filed on Jan. 10, 2019, which is specifically incorporated by reference herein for all that it discloses or teaches.

BACKGROUND

Handheld breath alcohol testing devices are useful in roadside estimation of blood alcohol level of drivers, workplace estimation of blood alcohol level of employees, and in other scenarios. Electrochemical sensors are commonly used in these devices to detect a concentration of alcohol in a sample of fluid. The sample of fluid (e.g., a breath sample, which may include gases, liquids, and mixtures thereof) is introduced into the electrochemical sensor and a current is generated by the oxidation of the alcohol within the fluid. The electrical output from the electrochemical sensor, plotted over time, forms an output curve, which may be used to estimate the concentration of alcohol in the fluid sample.

SUMMARY

Implementations described and claimed herein address the foregoing problems by providing a breath alcohol content device comprising an electrochemical sensor to convert an electrochemically convertible substance in a fluid sample to an electrical output on contact with the electrochemical sensor, a humidity sensor to detect water saturation level of the fluid sample, a microprocessor to calculate a quantity of the electrochemically convertible substance in the fluid sample using the electrical output from the electrochemical sensor and the detected water saturation level of the fluid sample, and a memory to store the calculated quantity of the electrochemically convertible substance.

Implementations described and claimed herein address the foregoing problems by further providing a wireless communication antenna. The microprocessor is further to monitor available wireless data networks via the wireless communication antenna, establish a wireless data connection with a pre-approved wireless network upon its detection, and upload the calculated quantity of the electrochemically convertible substance stored in the memory to network storage connected to the pre-approved wireless network.

Other implementations are also described and recited herein.

DETAILED DESCRIPTION

The technology disclosed herein includes various methods for determining the quantity of an electrochemically convertible substance in a fluid sample with a breath alcohol content device (or other fluid analysis apparatus). The fluid sample may be a gas, liquid, or a gas/liquid mixture (e.g., a breath sample, ambient air, a calibration standard, and so on). The disclosed technology involves measuring electrochemical (or fuel cell) sensor outputs to quantify alcohol content of the fluid sample.

Figure 1:
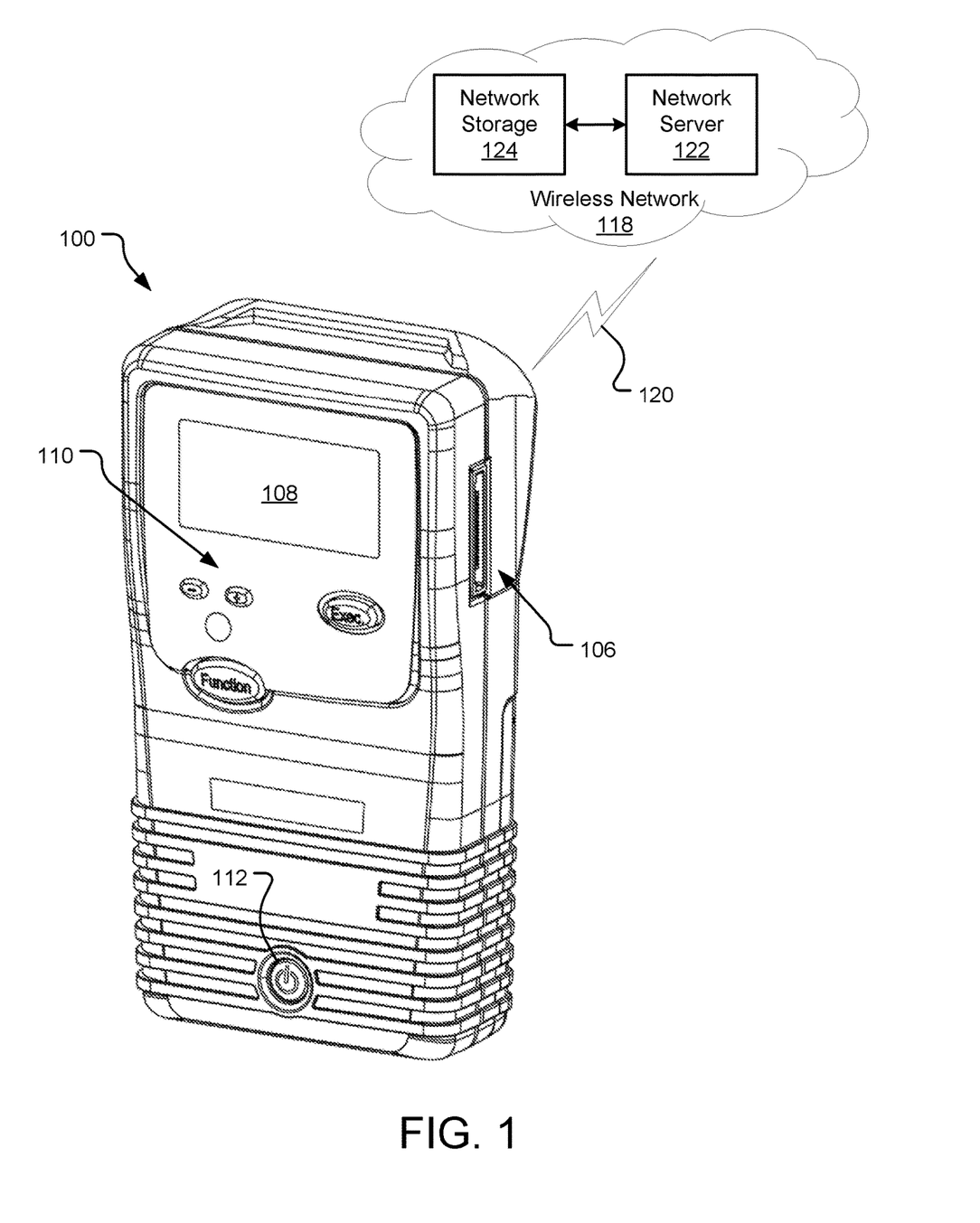
FIG. 1 is a front perspective view of an example breath alcohol content device incorporating the security and/or sensing functionalities disclosed herein.

FIG. 1 is a front perspective view of an example breath alcohol content device 100 incorporating security and/or sensing functionalities disclosed herein. During calibration checks or a recalibration process, a calibration standard fluid sample (not shown, see e.g., calibration standard fluid sample 226 of FIG. 2) is taken at a sample input (not shown, see e.g., sample input 202 of FIG. 2) of the device 100. During use, a fluid sample of a test subject's breath (not shown, see e.g., user breath sample 228 of FIG. 2) is also taken at the sample input of the device 100.

An electrochemically convertible substance in the fluid sample is converted in an electrochemical sensor (not shown, see e.g., electrochemical sensor 338 of FIG. 3) producing an electrical output. The electrical output is measured to produce sensor measurements for determining a quantity of the electrochemically convertible substance within the fluid sample. The determined quantity may be displayed on a display 108 (e.g., in the form of a percentage of alcohol in the fluid sample or a breath alcohol content measurement). The determined quantity may also be automatically or selectively stored in device memory (not shown, e.g., memory 304 of FIG. 3) for later retrieval. The device 100 may further include user input buttons 110, as well as an on/off power button 112. The display 108 may further be a touch screen with input, power, and/or other functions thereon.

Figure 3:
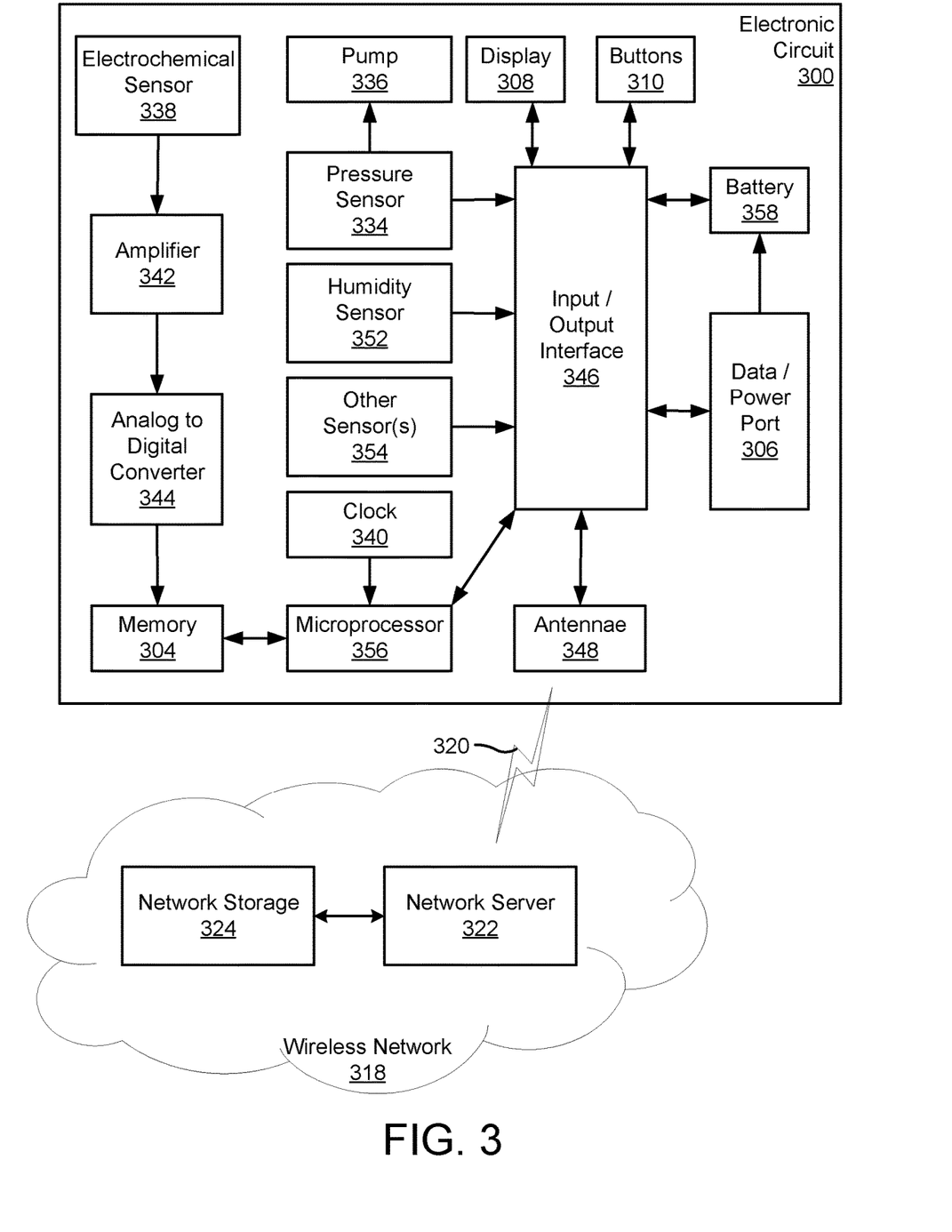
FIG. 3 is a block diagram showing an example electronic circuit of a breath alcohol content device incorporating the security and/or sensing functionalities disclosed herein.

The device 100 may further include a data/power port 106 that permits the device to be externally powered and charged to the extent that the device 100 includes onboard rechargeable batteries (not shown, see e.g., battery 358 of FIG. 3). The data/power port 106 also permits the device 100 to be physically connected to a network server 122 for data transfer operations. In other implementations, the data/power port 106 is separated into two distinct ports, one for power input and another for data transfer.

The device 100 may further be equipped with a wireless communication capability that allows the device 100 to establish a secured wireless connection 120 to a wireless network 118. The wireless network 118 also has a network server 122 and network storage 124 connected thereto. The device 100 may automatically upload sensor measurements from device memory to the network storage 124 upon establishing the secured wireless connection 120 to the network server 122. This upload may be accomplished without input from a device user and may also be performed without the device user's knowledge. The wireless network 118 may operate over a variety of communication standards (e.g., WIFI, Bluetooth, GPS, cellular) and over a variety of distances. In various implementations, the sensor measurements may be deleted or marked for deletion from the device memory upon successful uploading of the sensor measurements to the network storage 124.

In other implementations, the secured wireless connection 120 may also be used to manage the device 100 hardware and/or software, including but not limited to performing device health diagnostics, installing software updates, and downloading data collected by the device 100. In various implementations, these additional features may or may not be performed with device user input and may or may not occur with device user's knowledge.

In an example use case, a device user (e.g., a police officer) uses the device 100 to measure the intoxication level of a test subject. If the device 100 determines a controlled substance quantity that exceeds a threshold defined by law, the device user may take action to charge the test subject with a violation of the law, detain the test subject, and/or subject the test subject to further testing. If the device 100 determines the controlled substance quantity fails to exceed the threshold defined by law, the device user may subject the suspect to further testing and/or release the test subject.

As the action taken with regard to the test subject is dependent upon the device user, the device user may be subject to influence by the test subject or a $3^{rd}$ party (e.g., via bribery, persuasion, pity, etc.) to not take an appropriate action in response to the device 100 determining that the controlled substance quantity exceeds the threshold. In some implementations, the device 100 includes additional security functionalities to deter, discourage, and/or prevent the device user from taking an action inconsistent with the device output. More specifically, the additional security functionalities may prevent the user of the device 100 from intentionally disregarding or deleting a determined quantity reading from the device 100 or unintentionally disregarding (e.g., forgetting about) a determined quantity reading from the device 100.

For example, the device user may be denied access to the device memory and any and all determined quantities are automatically stored within the device memory as they are determined. Further, the device 100 may be equipped with wireless communication capability that will upload the determined quantities to the network storage 124 for processing without input from the user. Specifically, the device 100 may store an array of determined quantities, each with a timestamp, over time. When the device user returns to a central location (e.g., a police station), the device 100 may automatically detect the secured wireless network 118 and automatically upload the determined quantities to the network storage 124 via the network server 122 for processing. The determined quantities stored on the device 100 may then be marked for deletion, actively purged, and/or cycled out as new determined quantities are stored (e.g., first-in-first-out data purging).

In other implementations, the device 100 may maintain a cellular or GPS data signal while in use in the field and automatically upload the determined quantities to the network storage 124 as they are taken. In this implementation, the device 100 may omit or not utilize its internal memory to store the determined quantities, or the device 100 may also use its internal memory to store the determined quantities for redundancy.

In some implementations, the determined quantities are later checked against the device user's violation reporting mechanism (e.g., police reports) to check for any discrepancies. Further, automatically uploading the determined quantities may be a safeguard against allegations that the data was tampered with by the device user or a $3^{rd}$ party to the upload.

Figure 2:
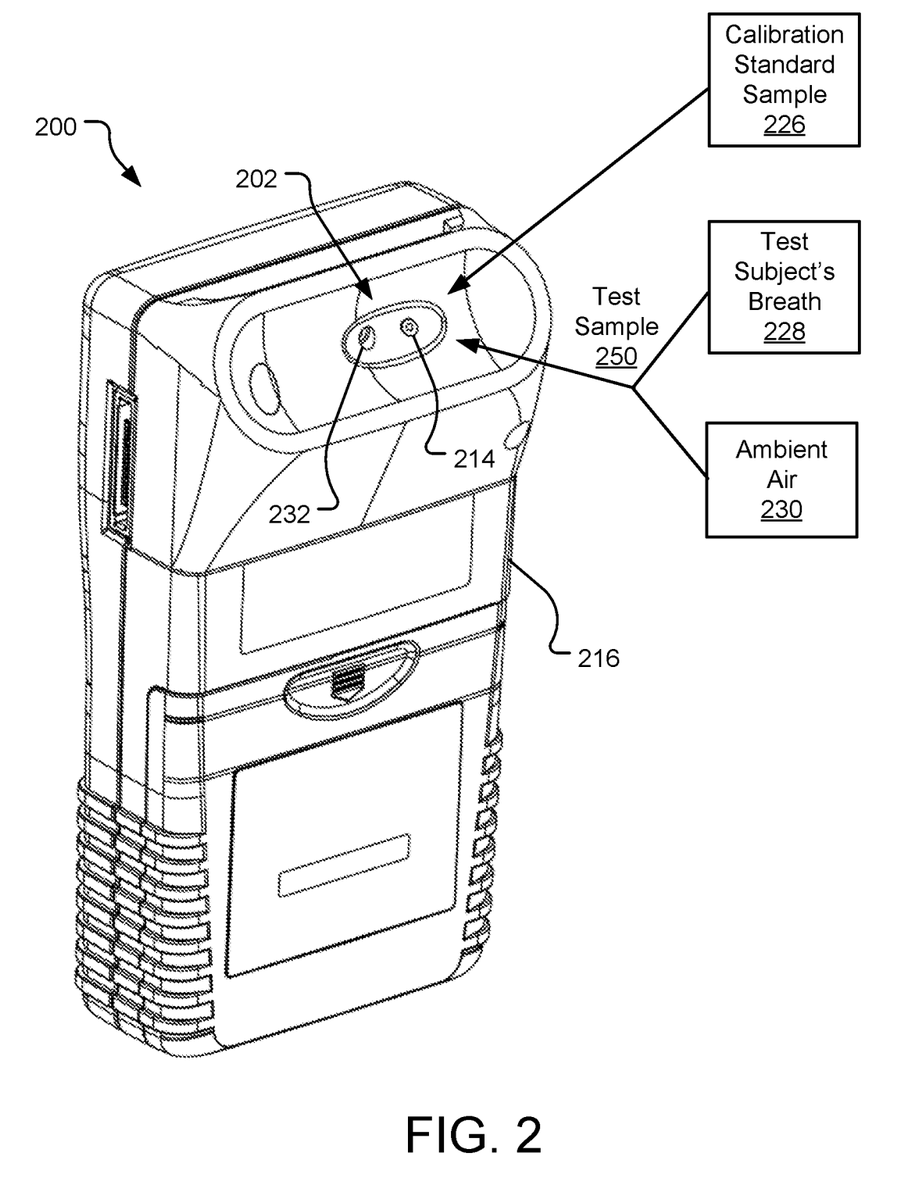
FIG. 2 is a rear perspective view of an example breath alcohol content device incorporating the security and/or sensing functionalities disclosed herein.

FIG. 2 is a rear perspective view of an example breath alcohol content device 200 incorporating security and/or sensing functionalities disclosed herein. During calibration checks or a recalibration process, a calibration standard fluid sample 226 is taken at the sample input 202 of the device 200. During use, a fluid test sample 250 of a test subject's breath 228 is also taken at sample input 202 of the device 200.

The sample input 202 may include a sample port 232 and a sensor port 214. The calibration standard fluid sample 226 or the fluid test sample 250 is drawn into the sample port 232 via a pump internal to the device 200 (not shown, see e.g., pump 336 of FIG. 3). The sample 226/250 then exits the device 200 via an exhaust port (not shown) in a housing 216 of the device 200. In some implementations, the device 200 does not include a dedicated exhaust port as the housing 216 may not be airtight. The sensor port 214 is connected to a humidity sensor (not shown, see e.g., humidity sensor 352 of FIG. 3) that permits additional sensing functionalities disclosed herein. In various implementations, the sensor port 214 may be connected to additional sensors (e.g., a pressure sensor and a temperature sensor). In other implementations, the sample port 232 and the sensor port 214 are combined into a singular physical port in the housing 216.

An electrochemically convertible substance in the sample 226/250 is converted in an electrochemical sensor (not shown, see e.g., electrochemical sensor 338 of FIG. 3) producing an electrical output. The electrical output is measured to produce sensor measurements for determining a quantity of the electrochemically convertible substance within the sample 226/228. The determined quantity may be displayed on a display (not shown, see e.g., display 108 of FIG. 1). The determined quantity may also be automatically or selectively stored in device memory (not shown, e.g., memory 304 of FIG. 3) for later retrieval.

In various implementations, the device 200 may be used to conduct active and/or passive sensor measurements. In an implementation where the device 200 is used to conduct active sensor measurements, a test subject places their mouth over the sample input 202 (or over a mouthpiece (not shown) attached to the sample input 202) and blows directly into the device 200. As a result, the entire sample collected by the sample port 232 and measured by the electrochemical sensor is the test subject's breath 228. This yields a consistent and accurate measurement of alcohol content of the test subject's breath 228.

In contrast, passive sensor measurements are performed by having a test subject blow at the sample input 202 without placing their mouth in contact with the sample input 202 or using a mouthpiece to ensure that the entire sample received by the sample port 232 is the test subject's breath 228. A portion of the sample collected by the sample port 232 is not the test subject's breath 228 as it mixes with ambient air 230 as it passes from the test subject's mouth to the sample port 232 without a seal therebetween.

In various implementations, a calculated quantity of the electrochemically convertible substance in the test subject's breath 228 using the aforementioned passive sensor measurements (or a passive test) is within approximately 12% (or approximately 25% or approximately 5%) of a similarly calculated quantity of the electrochemically convertible substance in the test subject's breath 228 actively collected via a mouthpiece attached to the breath alcohol content device (i.e., via active sensor measurements (or an active test). Approximately in the aforementioned context means+/−1%.

A pressure sensor (not shown, see e.g., pressure sensor 334 of FIG. 3) is located just inside the sensor port 214, which acts as a trigger for the device 200 to take a sample when it detects a slight increase in air pressure caused by the test subject blowing at the sample input 202. Passive sensor measurements are generally desirable as they may be taken quickly and from multiple test subjects without the need to change out mouthpieces or sanitize the sample input 202. Further, the test subjects may be more agreeable to the test if they don't have to physically contact the device 200 with their mouth. However, accurate determination of the alcohol content of the test subject's breath 228 typically suffers as compared to active sensor measurements because the test subject's breath 228 mixes with an unknown quantity of ambient air 230 prior to entering the sample port 232. This dilution factor typically renders passive sensor measurements as a pass/fail test rather than outputting an accurate reading of alcohol concentration in the test subject's breath.

In order to provide more accurate passive sensor measurements, the device 200 includes a humidity sensor (not shown, see e.g., humidity sensor 352 of FIG. 3) inside of the sensor port 214. The humidity sensor monitors ambient humidity (or water saturation level) over time to determine and track ambient air humidity level, which is less than that of the test subject's breath 228 in most environments. Further, the device 200 may be directed to pull a test blank of the ambient air 230 alone to determine ambient humidity immediately prior to performing a passive sensor measurement. In other implementations, the device 200 may pull a humidity level from a local weather service if connected to a cellular (or other) data network to determine ambient humidity. In still further implementations, the device 200 may have multiple humidity sensors, at least one inside the sensor port 214 for testing the humidity of the test sample 250 and at least one other oriented on an opposite side of the device 200 to monitor ambient humidity.

Upon detection of the increase in air pressure caused by the test subject blowing at the sample input 202, the humidity sensor takes another measurement of humidity that it associates with the test sample 250. Assuming that the test subject's breath is a saturated fluid, a microprocessor within the device 200 (not shown, see e.g., microprocessor 356 of FIG. 3) can calculate relative proportional content of the test sample 250 between the ambient air 230 and the test subject's breath 228. Once a proportion of the test sample 250 being the test subject's breath 228 is determined, the microprocessor can calculate breath alcohol content, correct for the proportion of the test sample 250 being the test subject's breath 228, and output a breath alcohol test result with accuracy comparable to an active sensor measurement, or at least better than a passive sensor measurement without humidity correction.

As example formula for calculating breath alcohol content in a passive test utilizing a humidity sensor is as follows.

$BrAC = \text{Measured sample } AC/f_B$; and $f_B = (H_S - H_A)/(H_B - H_A)$, where BrAC is the user's calculated breath alcohol content,
Measured sample AC is the measured sample's breath alcohol content (AC),
$f_B$ is fraction of the measured test sample that is the test subject's breath,
$H_S$ is the test sample humidity measurement,
$H_A$ is the ambient humidity measurement, and
$H_B$ is the test subject's breath humidity measurement (which may be assumed as 100%, or fully saturated).

Note that the formulae above utilize absolute humidity, while the humidity sensor may output relative humidity measurements. A conversion factor may need to be applied to convert measured relative humidity to absolute humidity prior to applying the formulae above. The device 200 may also include a temperature sensor (not shown, see e.g., other sensor(s) 354 of FIG. 3) inside the sensor port 214 to additionally track temperature and correctly apply a temperature-dependent conversion factor.

As discussed above, breath alcohol detectors or testers (e.g., the device 200) commonly use electrochemical sensors to measure the ethanol content of a test subject's breath. Such sensors have proven to be cost effective, accurate and highly immune to interfering substances, however, their performance may change over time. To ensure the device 200 continues to be accurate, it is periodically adjusted to a particular calibration standard.

One calibration standard known as a "wet bath" is achieved by using a solution of ethanol and water in a device called a simulator. Air is pumped or blown through the simulator where it picks up ethanol. The exhaust of the simulator provides a reliably precise ethanol gas mixture that is usable to test for accuracy and permits a user to calibrate and adjust the device 200 or a similar device. Simulators are not ideal, however, as they require power, take time to heat up, and are not very portable. In addition, the gas from a simulator changes as it is used due to the ethanol being depleted as the air is blown through the simulator.

Another calibration standard known as a "dry gas" is achieved by using a compressed cylinder-based ethanol and nitrogen mix having a highly accurate and precise gas mixture. Dry gas calibration standards offer excellent portability and accuracy without some of the drawbacks inherent with simulators, such as a power requirement, warm up time, etc.

Readings of dry gas cylinders using electrochemical sensors may produce a consistent offset of approximately −4% (or 4%, +/−1%) when compared to a wet bath calibration standard, complicating its use for testing and calibration. A device manufacturer may design around the offset by requiring an end user to select within the device 100 what type of calibration standard is used. The device then applies an approximately 4% correction factor or adjusts the concentration of the ethanol nitrogen mix to compensate for the approximately 4% offset.

The device 200 is periodically calibrated to ensure that it performs sensor measurements within a predefined range of accuracy. Calibration checks and recalibration procedures are typically performed at a lab where one or both of the wet bath and the dry gas calibration standards are available. The wet bath standard outputs a water saturated gas with which to test the device 200 calibration. The dry gas standard outputs a nearly completely water unsaturated gas with which to test the device 200 calibration. Prior art solutions require a lab technician to select on the device 200 whether the calibration standard used is a wet bath or a dry gas. This adds a step of complexity to the process, which consumes time and adds the potential that the lab technician makes an error in entering the wrong method. Further, the lab may utilize both methods for cross-checking purposes, which may frustrate a lab technician that is expected to change the device settings repeatedly as the testing method changes.

The humidity sensor described above may be used to detect which of the wet bath and dry gas standards is being used to calibrate the device 200 in real time, and without user input. This reduces the potential for user error in selecting the appropriate standard and may save time as a lab technician is not expected to change device settings for each test, or at least when the lab switches between the wet bath and dry gas standards.

FIG. 3 is a block diagram showing an example electronic circuit 300 of a breath alcohol content device (e.g., the breath alcohol content device 100 of FIG. 1) incorporating the security and/or sensing functionalities disclosed herein. A pressure sensor 334 may detect an increase in pressure at a sensor port (not shown, see e.g., sensor port 214 of FIG. 2) of the breath alcohol content device, which triggers pump 336 to pull a test sample into an electrochemical (or fuel cell) sensor 338. A microprocessor 356 reads a clock 340 and records a start time upon introduction of the test sample into the electrochemical sensor 338. An output of electrochemical sensor 338 is amplified by an amplifier 342 and may be conditioned to reduce noise and scale amplitude. The conditioned analog output is converted into a digital signal for analysis by analog to digital converter 344 and placed in device memory 304.

More specifically, at predefined periodic intervals beginning at the start time, the microprocessor 356 signals memory 304 to record sensor measurements. This signal causes the analog to digital converter 344 to latch the analog sensor output amplitude and the memory 304 to store a digital representation of the output amplitude, which may be a current or voltage value. The microprocessor 356 reads sensor measurements from the memory 304, determines a quantity of the electrochemically convertible substance within the fluid sample, and outputs the determined quantity back to the memory 304 or to an external memory or storage device.

An input/output (I/O) interface 346 provides a connection between the microprocessor 356 and the memory 304 and one or more user-interface devices (e.g., display 308, user input buttons 310, etc.), permitting communication of sensor measurements from the memory 304 to the user and/or permitting the user to provide instructions to the electronic circuit 300. The I/O interface 346 also may include a data/power port 306 that enables a physical data and/or power connection to the electronic circuit 300. The data/power port 306 may permit sensor measurements to be uploaded from the memory 304 and/or software updated to be downloaded to the memory 304. Further, the data/power port 306 may be used to charge battery 358, which may be used to power the breath alcohol content device.

In various implementations, the electronic circuit 300 also incorporates a wireless communication antenna 348 connected to the microprocessor 356 and the memory 304 via the I/O interface 346. The microprocessor 356 uses the antenna 348 to scan for an available and approved wireless network 318. Upon detection of the wireless network 318, the microprocessor 356 may establish a secured wireless connection 320 to a network server 322 within the wireless network 318 and network storage 324 connected thereto.

The microprocessor 356 may automatically upload sensor measurements from the measurement memory 304 to the network storage 324 upon establishing the secured wireless connection 320 to the network server 322. This upload may be accomplished without input from a user of the electronic circuit 300 and may also be performed without the user's knowledge. This upload may also be encrypted to prevent tampering with the uploaded data, or to address privacy concerns. The wireless network 318 may operate over a variety of communication standards (e.g., WIFI, Bluetooth, GPS, cellular) and over a variety of distances. In various implementations, the sensor measurements may be deleted or marked for deletion from the memory 304 upon successful uploading of the sensor measurements to the network storage 324.

In other implementations, the secured wireless connection 320 may also be used to manage the electronic circuit 300 and an associated device remotely, including but not limited to performing device health diagnostics, installing software updates, and downloading data collected by the electronic circuit 300. In various implementations, these additional features may or may not be performed with user input and may or may not occur with user knowledge.

The electronic circuit 300 may also be used to take a passive sensor measurement, as described above with reference to FIG. 2. A pressure sensor 334 is located just inside a sample port (not shown, see e.g., sample port 232 of FIG. 2), which acts as a trigger for the electronic circuit 300 to take a sample when it detects a slight increase in air pressure caused by a user blowing on the sample port. In order to provide more accurate passive sensor measurements, the electronic circuit 300 includes a humidity sensor 352 inside an adjacent sensor port (not shown, see e.g., sensor port 214 of FIG. 2). The humidity sensor 352 monitors ambient humidity over time to determine and track ambient air humidity level, which is less than that of the test subject's breath in most environments. In some implementations, other sensors 354 track additional environmental factors that may affect the passive sensor measurement (e.g., temperature and barometric pressure).

Upon detection of a rapid increase in air pressure caused by a user blowing on the sample port (e.g., via a barometric pressure sensor 354), the humidity sensor 352 takes another measurement of humidity that it associates with the user's test sample. Assuming that the test subject's breath is a saturated fluid, the microprocessor 356 calculates relative proportional content of the test sample between ambient air and the test subject's breath. Once a proportion of the sample being the test subject's breath is determined, the microprocessor 356 can calculate breath alcohol content, correct for the proportion of the sample being the test subject's breath, and output a breath alcohol test result with accuracy comparable to the active sensor measurement, or at least better than the passive sensor measurement without humidity correction. In various implementations, device sensors for pressure, humidity, and temperature may be combined into a singular instrument having a singular port or multiple ports, or separated into different instruments, or some combination thereof.

The electronic circuit 300 may also be used to calibrate an associated breath alcohol content device, as described above with reference to breath alcohol content device 200 of FIG. 2. The humidity sensor 352 may be used to detect which of wet bath and dry gas standards is being used to calibrate the device in real time, and without user input. As the wet bath standard is a water saturated gas and the dry gas standard is a nearly completely water unsaturated gas, the humidity sensor 352 may distinguish between the two. For example, the humidity sensor 352 may focus on the slope of a humidity curve over time. The microprocessor 356 may assume that the calibration standard is a wet bath until the slope of the humidity curve drops rapidly toward 0%. Such a drop would trigger the microprocessor 356 to select the dry gas standard. In another implementation, humidity level ranges are set for each of the calibration methods (e.g., 0-10% for a dry gas standard and 90-100% for a wet bath standard). The microprocessor 356 selects the appropriate standard based on the detected humidity level. This example also provides for an erroneous humidity level (e.g., 11%-89%), which may indicate a problem with the testing apparatus and an instruction to the lab technician to check the equipment, and perhaps an automatic invalidation of an associated test.

A separate computing system (e.g., network server 322) may also be used to implement some of the functional aspects of the electronic circuit 300 or add additional functional aspects. The computer system may be capable of executing a computer program product embodied in a tangible computer-readable storage medium to execute a computer process. Data and program files may be input to the computer system, which reads the files and executes the programs therein using one or more processors. Some of the elements of the computer system may include an I/O section, a central processing unit (e.g., processor), and a program memory. There may be one or more processors, such that the processor of the computer system comprises a single central processing unit, or a plurality of processing units, commonly referred to as a parallel processing environment. The computer system may be a conventional computer, a distributed computer, or any other type of computer. The described technology is optionally implemented in software loaded in memory stored on a storage unit, and/or communicated via a wired or wireless network link on a carrier signal, thereby transforming the computer system to a special purpose machine for implementing the described operations.

The I/O section in the computer system may be connected to one or more user-interface devices (e.g., a breath alcohol content device, a keyboard, a display unit, etc.) and/or storage units (e.g., network storage 324, other storage drives, memory, etc.). Computer program products containing mechanisms to effectuate the systems and methods in accordance with the described technology may reside in the storage unit(s) of such a system.

A communication interface may be capable of connecting the computer system and/or the electronic circuit 300 to the wireless network 318, through which the computer system and/or the electronic circuit 300 can receive instructions and data embodied in a carrier wave. When used in a local-area-networking (LAN) environment, the computer system is connected (by wired connection or wirelessly) to a local network through the network interface or adapter, which is one type of communications device. When used in a wide-area-networking (WAN) environment, the computer system typically includes a modem, a network adapter, or any other type of communications device for establishing communications over the wide area network. In a networked environment, program modules depicted relative to the computer system or portions thereof, may be stored in a remote memory storage device. It is appreciated that the network connections described are exemplary and other means of and communications devices for establishing a communications link between the computer system, the electronic circuit 300, and the wireless network 318 may be used.

In an example implementation, a user interface software module and other modules may be embodied by instructions stored in memory (e.g., memory 304) and/or a storage unit and executed by a processor (e.g., microprocessor 356). Further, local computing systems, remote data sources and/or services, and other associated logic represent firmware, hardware, and/or software may be configured to assist in obtaining breath alcohol content measurements. A breath alcohol content computer process may be implemented using a general purpose computer and specialized software (such as a server executing service software), a special purpose computing system and specialized software (such as a mobile device or network appliance executing service software), or other computing configurations. In addition, breath alcohol content measurements and computations may be stored in the memory 304 and executed by the microprocessor 356.

It should be understood that the breath alcohol content computer process may be implemented in software executing on a stand-alone computer system, whether connected to a breath alcohol content device or not. In yet another implementation, the breath alcohol content computer process may be integrated into a device (e.g., a breath alcohol content device).

Data storage and/or memory may be embodied by various types of storage, such as hard disk media, a storage array containing multiple storage devices, optical media, solid-state drive technology, read-only memory (ROM), random access memory (RAM), and other technology. The operations may be implemented in firmware, software, hard-wired circuitry, gate array technology and other technologies, whether executed or assisted by a microprocessor, a microprocessor core, a microcontroller, special purpose circuitry, or other processing technologies.

For purposes of this description and meaning of the claims, the terms "computer readable storage media" and "memory" refer to a tangible (or non-transitory) data storage device, including non-volatile memories (such as flash memory, disc drives, and the like) and volatile memories (such as dynamic random-access memory and the like). The computer instructions either permanently or temporarily reside in the memory, along with other information such as data, virtual mappings, operating systems, applications, and the like that are accessed by a computer processor to perform the desired functionality. The terms "computer readable storage media" and "memory" expressly do not include a transitory medium such as a carrier signal, but the computer instructions can be transferred to the memory wirelessly.

Figure 4:
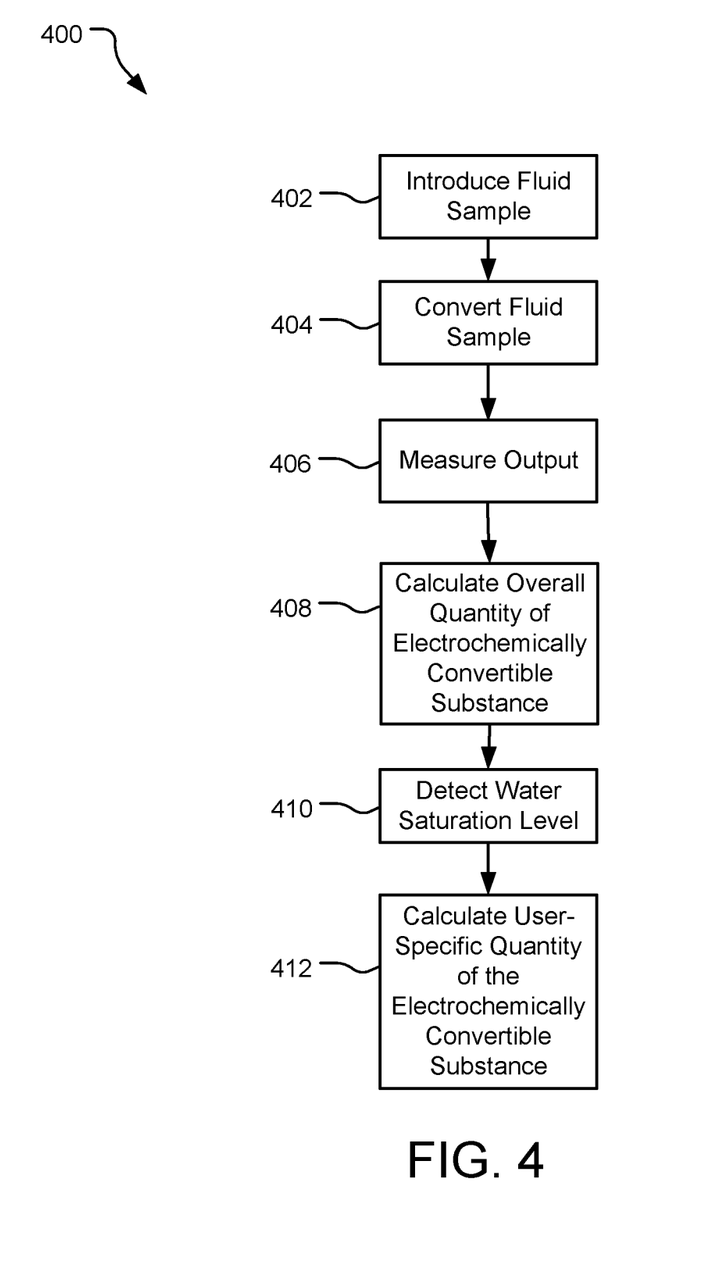
FIG. 4 is a flowchart of example operations for determining the quantity of an electrochemically convertible substance in a fluid sample including a mixture of a test subject's breath and ambient air.

FIG. 4 is a flowchart of example operations 400 for determining the quantity of an electrochemically convertible substance in a fluid sample including a mixture of a test subject's breath and ambient air. In various implementations, a user selects a test mode on a breath alcohol sensing device prior to the breath alcohol sensing device performing operations 400.

Introducing operation 402 introduces a fluid sample into an electrochemical sensor. Introducing operation 402 may be performed by a user breathing into the breath alcohol sensing device in a passive test, for example. The passive test may introduce an unknown quantity of ambient air along with the test subject's breath into the breath alcohol sensing device. The test subject's breath passes adjacent to the electrochemical sensor within the breath alcohol sensing device.

Conversion operation 404 electrochemically converts at least a portion of the fluid sample into an electrical output from the electrochemical sensor. In various implementations, the electrochemical sensor is a fuel cell device that uses alcohol content in the fluid sample to vary the output of the fuel cell. Measuring operation 406 measures the electrical output from the electrochemical sensor on a periodic basis to produce sensor measurements. Calculating operation 408 sums the area under the electrochemical sensor output curve to calculate the overall quantity of the electrochemically convertible substance within the fluid sample. In various implementations, the calculated quantities may be stored in a memory for further analysis.

Detection operation 410 detects a water saturation level within the fluid sample. As the test subject's breath is completely or nearly-completely saturated fluid and the ambient air is typically less than fully saturated, the detection operation 410 may be used to find a proportion of the fluid sample that is the test subject's breath vs. the ambient air. Calculating operation 412 calculates a user-specific quantity of the electrochemically convertible substance within the fluid sample. More specifically, the calculating operation 412 uses the results from the detection operation 410 to determine how much of the fluid sample is the test subject's breath and adjusts the previously calculated overall quantity of the electrochemically convertible substance within the fluid sample to apply exclusively to the test subject's breath. In other words, the calculating operation 412 both calculates a proportion of the fluid sample that constitutes the test subject's breath based on the detected water saturation level of the fluid sample and calculates a quantity of the electrochemically convertible substance within the test subject's breath based on the calculated quantity of the electrochemically convertible substance in the fluid sample and the proportion of the fluid sample that is the test subject's breath.

Figure 5:
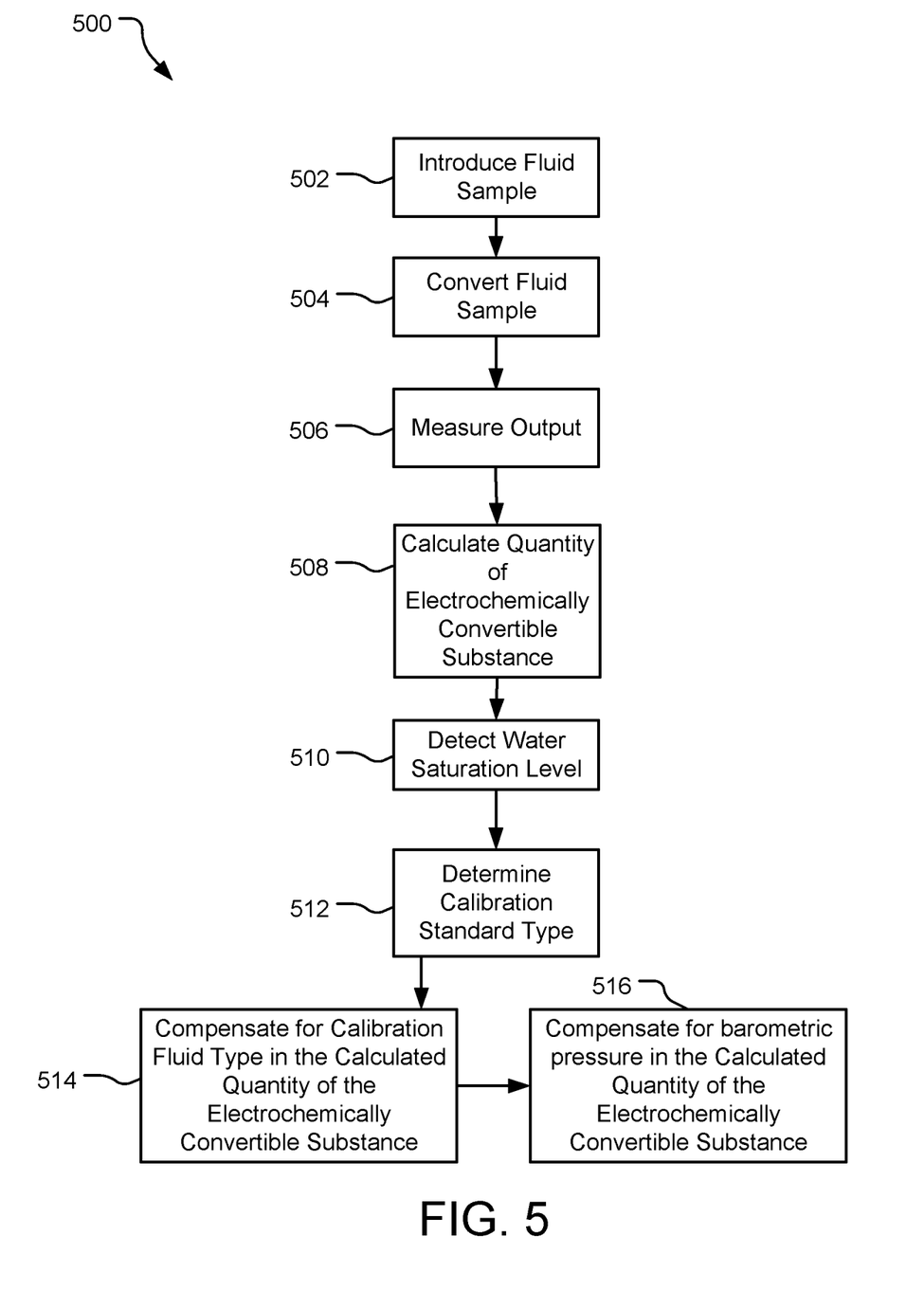
FIG. 5 is a flowchart of example operations for determining the quantity of an electrochemically convertible substance in a dry gas or a wet bath calibration fluid sample.

FIG. 5 is a flowchart of example operations 500 for determining the quantity of an electrochemically convertible substance in a dry gas or wet bath calibration standard fluid sample. In various implementations, a user selects a calibration check mode or recalibration mode on a breath alcohol sensing device prior to the breath alcohol sensing device performing operations 500. The calibration check mode checks the ability of the breath alcohol sensing device to detect the alcohol content of a known calibration standard within a predetermined tolerance. The recalibration mode resets the detected alcohol content of a known calibration standard to equal that of the calibration standard. In some implementations, the recalibration mode may automatically or manually follow a failed calibration check.

Introducing operation 502 introduces a fluid sample into an electrochemical sensor. Introducing operation 502 may be performed by connecting the breath alcohol sensing device to one of a dry gas or a wet bath calibration standard, for example. A sample from the calibration standard passes adjacent to the electrochemical sensor within the breath alcohol sensing device for purposes of calibrating the device for later use in the field.

Conversion operation 504 electrochemically converts at least a portion of the fluid sample into an electrical output from the electrochemical sensor. In various implementations, the electrochemical sensor is a fuel cell device that uses alcohol content in the fluid sample to vary the output of the fuel cell. Measuring operation 506 measures the electrical output from the electrochemical sensor on a periodic basis to produce sensor measurements.

A calculating operation 508 sums the area under the electrochemical sensor output curve to calculate the quantity of the electrochemically convertible substance within the fluid sample. In various implementations, the calculated quantities may be stored in a memory for further analysis. Further, the breath alcohol sensing device may receive from the user an alcohol concentration of the dry gas or wet bath calibration standard for use in the calculating operation 508. Alternatively, a common alcohol concentration from each of the dry gas and wet bath calibration standards is stored within the breath alcohol sensing device and applied automatically for the dry gas or wet bath calibration standard, as appropriate.

Detection operation 510 detects water saturation level within the fluid sample. Determining operation 512 determines the calibration fluid type. As the dry gas calibration standard is typically unsaturated or nearly unsaturated and the wet bath calibration standard is typically fully saturated or nearly fully saturated, the detected water saturation level distinguishes between the two calibration standards.

Compensating operation 514 compensates the previously calculated quantity of the electrochemically convertible substance within the fluid sample for the determined calibration standard. The net result is an accurate calibration of the breath alcohol sensing device without input from the user regarding calibration standard type.

A further compensation operation 516 may be performed if the determined calibration standard type is a dry gas calibration standard. As dry gas calibration standards are filled at a time and location having a first ambient barometric pressure (e.g., at sea level) and then later used to calibrate the breath alcohol sensing device at a different time and in a different location having a potentially significantly different second barometric pressure (e.g., at a significant elevation), the further compensation operation 516 corrects the previously calculated quantity of the electrochemically convertible substance within the fluid sample for any difference in ambient barometric pressure.

Figure 6:
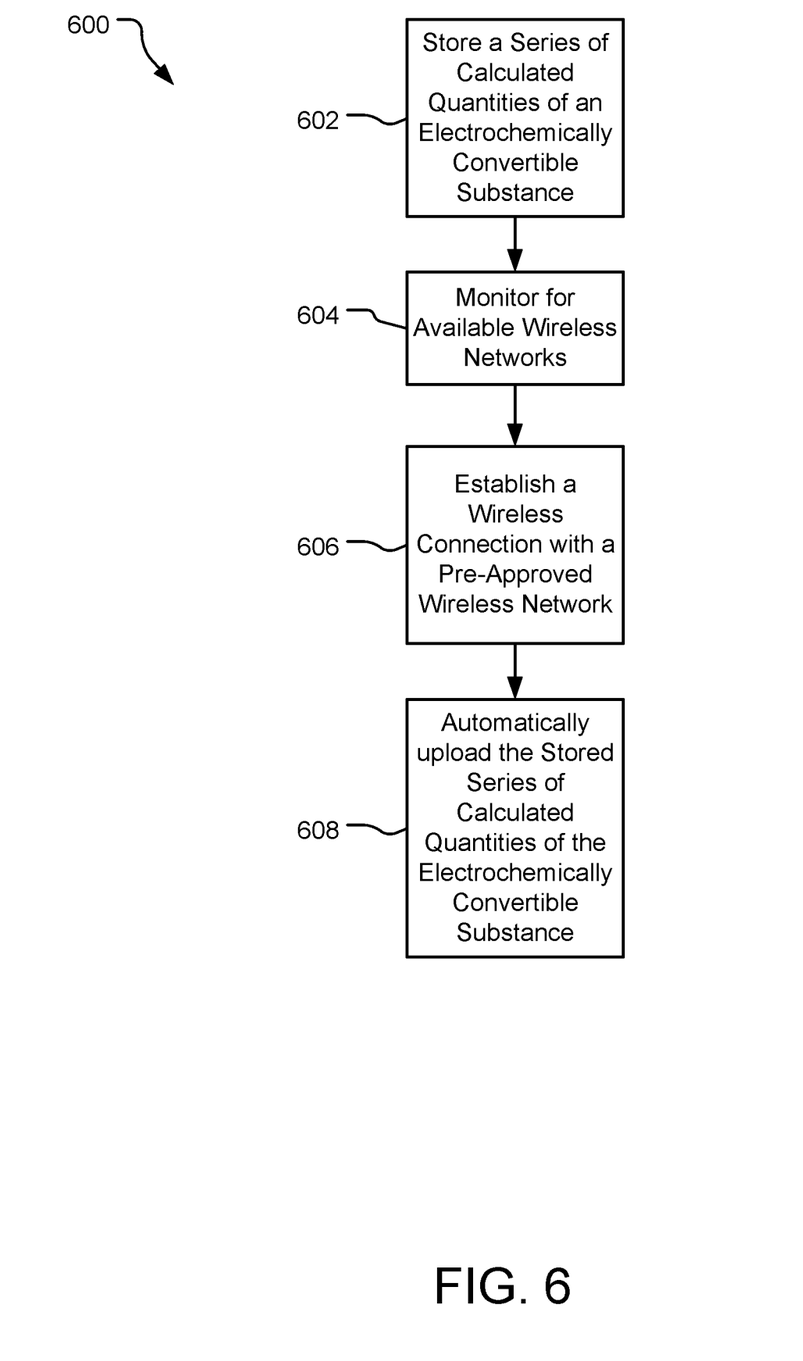
FIG. 6 is a flowchart of example operations for uploading stored quantities of an electrochemically convertible substance from a breath alcohol tester to network storage.

FIG. 6 is a flowchart of example operations 600 for uploading stored quantities of an electrochemically convertible substance from a breath alcohol content device to network storage. A storing operation 602 stores a series of calculated quantities of the electrochemically convertible substance of a series of fluid samples on a breath alcohol content device. Each stored value is associated with a test subject, though multiple stored entries may be associated with the same test subject.

A monitoring operation 604 monitors for available wireless data networks. For example, in an implementation where the breath alcohol content device includes a WIFI interface, the breath alcohol content device is monitoring for available WIFI networks. An establishing operation 606 establishes a wireless connection with a pre-approved wireless network, should such a network become available. The pre-approved wireless network is a wireless network that the device may been previously instructed to trust with sensitive information stored on the breath alcohol content device.

An uploading operation 608 automatically uploads the stored series of calculated quantities of the electrochemically convertible substance to a data storage device within the wireless data network. In other implementations, the uploading operation 608 automatically uploads each quantity of the electrochemically convertible substance as it is calculated, so long as the breath alcohol content device remains connected to the pre-approved wireless network. The uploading operation 608 may occur without the instruction and/or knowledge of a user of the breath alcohol content device. The uploading operation 608 also include a time stamp of when the fluid sample was taken and/or a location stamp (e.g., via a global positioning system (GPS) signal) of where the fluid sample was taken. The data on the data storage device may then be actively deleted or marked as approved for deletion as the data is now stored and secured on the data storage device within the wireless data network.

In some implementations, each of the calculated quantities of the electrochemically convertible substance is only viewable by the user of the breath alcohol content device after the uploading operation 608 is complete. This reduces the opportunity for the user to be coerced into preventing the uploading operation 608 from occurring (e.g., by destroying the breath alcohol content device).

The implementations of the invention described herein are implemented as logical steps in one or more computer systems. The logical operations of the present invention are implemented (1) as a sequence of processor-implemented steps executed in one or more computer systems and (2) as interconnected machine or circuit modules within one or more computer systems. The implementation is a matter of choice, dependent on the performance requirements of the computer system implementing the invention. Accordingly, the logical operations making up the embodiments of the invention described herein are referred to variously as operations, steps, objects, or modules. Furthermore, it should be understood that logical operations may be performed in any order, adding and omitting as desired, unless explicitly claimed otherwise or a specific order is inherently necessitated by the claim language.

The above specification, examples, and data provide a complete description of the structure and use of example implementations of the invention. Since many implementations of the invention can be made without departing from the spirit and scope of the invention, the invention resides in the claims hereinafter appended. Furthermore, structural features of the different implementations may be combined in yet another implementation without departing from the recited claims. The implementations described above and other implementations are within the scope of the following claims.

What is claimed is:

1. A breath alcohol content device comprising:
   an electrochemical sensor to convert an electrochemically convertible substance in a fluid sample to an electrical output on contact with the electrochemical sensor, wherein the fluid sample is a dry gas calibration standard or a wet bath calibration standard;
   a humidity sensor to detect water saturation level of the fluid sample; and
   a microprocessor to:
      determine which of the dry gas calibration standard and the wet bath calibration standard constitutes the fluid sample based on the detected water saturation level of the fluid sample; and
      calculate a quantity of the electrochemically convertible substance in the fluid sample using the electrical output from the electrochemical sensor and the detected water saturation level of the fluid sample, automatically compensating for the determined calibration standard of the fluid sample.

2. The breath alcohol content device of claim 1, wherein the fluid sample is passively collected via a sample port in the breath alcohol content device.

3. The breath alcohol content device of claim 1, further comprising:
   a barometric pressure sensor to detect an ambient barometric pressure, the microprocessor further instructed to compensate for the ambient barometric pressure in calculating the quantity of the electrochemically convertible substance in the fluid sample when the dry gas calibration standard constitutes the fluid sample.

4. The breath alcohol content device of claim 1, wherein the determined calibration standard is dry gas when the water saturation level of the fluid sample is less than 10%.

5. The breath alcohol content device of claim 1, wherein the determined calibration standard is wet bath when the water saturation level of the fluid sample is greater than 90%.

6. The breath alcohol content device of claim 1, wherein a difference in electrical output from the electrochemical sensor between the dry gas calibration standard and the wet bath calibration standard is approximately 4%.

7. The breath alcohol content device of claim 1, further comprising:
   a pump to draw the fluid sample into the breath alcohol content device; and
   a barometric pressure sensor, the microprocessor further instructed to trigger the pump to draw the fluid sample into the breath alcohol content device upon detection of a rapid increase in barometric pressure.

8. The breath alcohol content device of claim 1, further comprising:
   a memory to store the calculated quantity of the electrochemically convertible substance.

9. The breath alcohol content device of claim 8, further comprising:
   a wireless communication antenna, wherein the microprocessor is further instructed to monitor available wireless data networks via the wireless communication antenna, establish a wireless data connection with a pre-approved wireless network upon its detection, and upload the calculated quantity of the electrochemically convertible substance stored in the memory to network storage connected to the pre-approved wireless network.

10. The breath alcohol content device of claim 9, wherein establishing the wireless data connection and uploading the calculated quantity of the electrochemically convertible substance is performed without user input.

11. The breath alcohol content device of claim 9, wherein the microprocessor encrypts the calculated quantity of the electrochemically convertible substance prior to uploading to the pre-approved wireless network.

12. The breath alcohol content device of claim 9, wherein the microprocessor one of marks for deletion and actively deletes the calculated quantity of the electrochemically convertible substance from the memory following a successful upload to the network storage.

13. The breath alcohol content device of claim 9, wherein the uploaded quantity of the electrochemically convertible substance includes a time stamp of when the fluid sample was taken and a location stamp of where the fluid sample was taken.

14. The breath alcohol content device of claim 9, further comprising:
   a display, wherein the calculated quantity of the electrochemically convertible substance is displayed to a user after the microprocessor uploads the calculated quantity of the electrochemically convertible substance to the network storage.

15. The breath alcohol content device of claim 9, wherein the microprocessor is further instructed to download software updates for the breath alcohol content device from the pre-approved wireless network.

16. A method of determining a quantity of an electrochemically convertible substance in a fluid sample comprising:
   converting the electrochemically convertible substance in the fluid sample to an electrical output on contact with an electrochemical sensor, wherein the fluid sample is a dry gas calibration standard or a wet bath calibration standard;
   detecting a water saturation level of the fluid sample;

determining which of the dry gas calibration standard and the wet bath calibration standard constitutes the fluid sample based on the detected water saturation level of the fluid sample; and calculating the quantity of the electrochemically convertible substance in the fluid sample using the electrical output from the electrochemical sensor and the detected water saturation level of the fluid sample, automatically compensating for the determined calibration standard of the fluid sample.

17. The method of claim 16, further comprising:
storing the calculated quantity of the electrochemically convertible substance in memory.

18. The method of claim 16, further comprising:
monitoring available wireless data networks via a wireless communication antenna;
establishing a wireless data connection with a pre-approved wireless network upon its detection; and
uploading the calculated quantity of the electrochemically convertible substance including a time stamp of when the fluid sample was taken and a location stamp of where the fluid sample was taken to network storage connected to the pre-approved wireless network.

19. One or more computer-readable storage media encoding computer-executable instructions for executing on a computer system a computer process for determining a quantity of an electrochemically convertible substance in a fluid sample, the computer process comprising:
converting the electrochemically convertible substance in the fluid sample to an electrical output on contact with an electrochemical sensor, wherein the fluid sample is a dry gas calibration standard or a wet bath calibration standard;
detecting a water saturation level of the fluid sample;
determining which of the dry gas calibration standard and the wet bath calibration standard constitutes the fluid sample based on the detected water saturation level of the fluid sample; and
calculating the quantity of the electrochemically convertible substance in the fluid sample using the electrical output from the electrochemical sensor and the detected water saturation level of the fluid sample, automatically compensating for the determined calibration standard of the fluid sample.

20. The one or more computer-readable storage media of claim 19, wherein the computer process further comprises:
storing the calculated quantity of the electrochemically convertible substance in memory;
monitoring available wireless data networks via a wireless communication antenna;
establishing a wireless data connection with a pre-approved wireless network upon its detection; and
uploading the calculated quantity of the electrochemically convertible substance stored in the memory including a time stamp of when the fluid sample was taken and a location stamp of where the fluid sample was taken to network storage connected to the pre-approved wireless network.

21. The breath alcohol content device of claim 1, wherein a second fluid sample includes a mixture of a test subject's breath and ambient air, wherein the microprocessor is further to:
determine a proportion of the second fluid sample that constitutes the test subject's breath using a fractional calculation of the detected water saturation level of the second fluid sample; and
calculate a quantity of the electrochemically convertible substance within the test subject's breath based on the calculated quantity of the electrochemically convertible substance in the second fluid sample and the determined proportion of the second fluid sample that constitutes the test subject's breath.

22. The breath alcohol content device of claim 21, wherein a calculated quantity of the electrochemically convertible substance in the test subject's breath based on the fluid proportion of the fluid sample that is the test subject's breath is within approximately 12% of a similarly calculated quantity of the electrochemically convertible substance in the test subject's breath actively collected via a mouthpiece attached to the breath alcohol content device.

23. The method of claim 16, wherein a second fluid sample includes a mixture of a test subject's breath and ambient air, the method further comprising:
determining a proportion of the second fluid sample that constitutes the test subject's breath using a fractional calculation of the detected water saturation level of the second fluid sample; and
calculating a quantity of the electrochemically convertible substance within the test subject's breath based on the calculated quantity of the electrochemically convertible substance in the second fluid sample and the determined proportion of the second fluid sample that constitutes the test subject's breath.

24. The method of claim 16, wherein establishing the wireless data connection and uploading the calculated quantity of the electrochemically convertible substance is performed without user input.

25. The one or more computer-readable storage media of claim 19, wherein the second fluid sample includes a mixture of a test subject's breath and ambient air, and wherein the computer process further comprises:
determining a proportion of the second fluid sample that constitutes the test subject's breath using a fractional calculation of the detected water saturation level of the second fluid sample; and
calculating a quantity of the electrochemically convertible substance within the test subject's breath based on the calculated quantity of the electrochemically convertible substance in the second fluid sample and the determined proportion of the second fluid sample that constitutes the test subject's breath.

* * * * *